United States Patent [19]

Conrow et al.

[11] 3,998,957
[45] Dec. 21, 1976

[54] COMPLEMENT INHIBITORS

[75] Inventors: Ransom Brown Conrow, Pearl River; Seymour Bernstein, New City, both of N.Y.

[73] Assignee: American Cyanamid Company, Stamford, Conn.

[22] Filed: Dec. 12, 1975

[21] Appl. No.: 640,370

[52] U.S. Cl. .......................... 424/273; 260/308 B
[51] Int. Cl.² .................................. C07D 249/22
[58] Field of Search ............... 260/308 B; 424/269, 424/273

[56] References Cited

UNITED STATES PATENTS 3,895,027  7/1975  Katner ..................... 260/310 R

OTHER PUBLICATIONS

Fong et al., Chemical Abstracts, vol. 76 (1972), 148,766w.

*Primary Examiner*—Paul M. Coughlan, Jr.
*Attorney, Agent, or Firm*—Jack W. Richards

[57] ABSTRACT

1,1'-[ureylenebis(sulfo-p-phenylene)]bis{sulfo-1H,8H-indazolo[2,3,4-cde]benzotriazol-9-ium hydroxide},bis(inner salts), tetra salts useful as complement inhibitors.

7 Claims, No Drawings

COMPLEMENT INHIBITORS

BACKGROUND OF THE INVENTION

The present invention resides in the concept of certain 1,1'-[ureylenebis(sulfo-p-phenylene)]bis{sulfo-1H, 8H-indazolo[2,3,4-cde]benzotriazol-9-ium -hydroxide},bis(inner salts), tetra salts and their use as inhibitors of the complement system of warm-blooded animals.

The term "complement" refers to a complex group of proteins in body fluids that, working together with antibodies or other factors, play an important role as mediators of immune, allergic, immunochemical and-/or immunopathological reactions. The reactions in which complement participates take place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in body processes can be found in, for example, Bull. World Health Org., 39 935–938 (1968); Scientific American, 229, (No. 5), 54–66 (1973); Medical World News, Oct. 11, 1974. pp. 53–58; 64–66; Harvey Lectures, 66, 75–104 (1972); *The New England Journal of Medicine*, 287, 489–495, 545–549, 592–596, 642–646 (1972); *The John Hopkins Med. J.* 128, 57–74 (1971); and Federation Proceedings, 32, 134–137 (1973).

The complement system can be considered to consist of three sub-systems: (1) a recognition unit (C1q) which enables it to combine with antibody molecules that have detected a foreign invader; (2) an activation unit (C1r, C1s, C2, C4, C3), which prepares a site on the neighboring membrane; and (3) an attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host'cells. Immunity is therefore a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease, in which the disease symptoms are caused by pathological effects of the immune system in the host's tissues. In summary, the complement system has been shown to be involved with inflamation, coagulation, fibrinolysis, antibody-antigen reactions and other metabolic processess.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection, it also results in inflammation and tissue damage in the immunopathological process. The nature of certain of the complement proteins, suggestions regarding the mode of complement binding to biological membranes and the manner in which complement effects membrane damage are discussed in Annual Review in Biochemistry, 38, 389 (1969).

A variety of substances have been disclosed as inhibiting the complement system, i.e., as complement inhibitors. For example, the compounds 3,3'-ureylenebis[6-(2-amino-8-hydroxy-6-sulfo-1-naphthylazo)]benzenesulfonic acid tetrasodium salt (chlorazol fast pink), heparin and a sulphated dextran have been reported to hane an anticomplementary effect, *British Journal of Experimental Pathology*, 33, 327–339 (1952). The compound 8,8'-[ureylenebis[m-phenylenecarbonylimino(4-methyl-m-
-phenylene)carbonylimino]]di-1,3,5-naphthalenetrisulfonic acid, hexasodium salt (Suramin Sodium) is described as a competitive inhibitor of the complement system, *Clin. Exp. Immunol.*, 10, 127–138 (1972). German Patent No. 2,254,893 or South African Patent No. 727,923 discloses certain 1-diphenylmethyl-4-(3-phenylallyl)piperazines useful as complement inhibitors. Other chemical compounds having complement inhibiting activity are disclosed in, for example, *Journal of Medicinal Chemistry*, 12, 415–419, 902–905, 1049–1052, 1053–1056 (1969); *Canadian Journal of Biochemistry*, 47, 547–552 (1969); *The Journal of Immunology*, 93, 629–540 (1964); *The Journal of Immunology*, 104, 279–288 (1970); *The Journal of Immunology*, 106, 241–245 (1971); *The Journal of Immunology*, 111, 1061–1066 (1973).

It has been reported that the known complement inhibitors epsilon-aminocaproic acid, Suramin Sodium and tranexamic acid have been used with success in the treatment of hereditary angioneurotic edema, a disease state resulting from an inherited deficiency or lack of function of the serum inhibitor of the activated first component of complement (C1 inhibitor), The New England Journal of Medicine, 286, 808–812 (1972); Allergol, Et. Immunopath, II, 163–168 (1974); and *J. Allergy Clin. Immunol.*, 53, No. 5, 298–302 (1974).

SUMMARY OF THE INVENTION

It has now been discovered that a representative 1,1'-[ureylenebis(sulfo-p-phenylene)]bis{sulfo-1H,8-H-indazolo--[2,3,4-cde]-benzotriazol-9-ium hydroxide}, bis (inner salt), tetra salt interacts with the complement reaction sequence, thereby inhibiting complement activity in body fluids.

This invention is particularly concerned with compounds having complement inhibiting activity of the general formula (I):

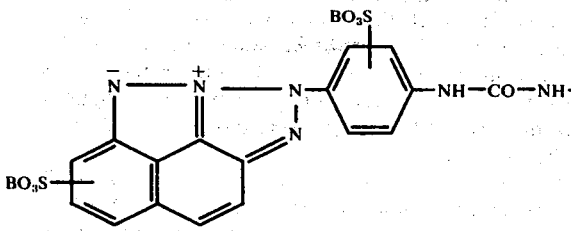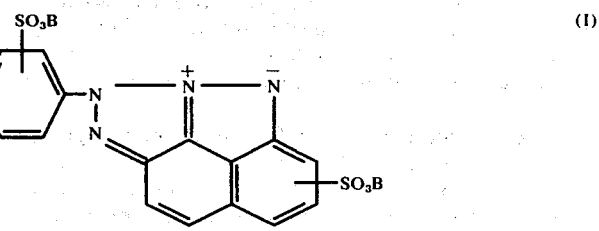

(I)

wherein B is Na (sodium) or K (potassium), with the proviso that each B is identical in the same compound.

Of particular interest in the above general formula (I) are the group of compounds wherein B is Na and, within this group, the compound of most interest is 1,1'-[ureylenebis(2-
-sulfo-p-phenylene)]bis{6-sulfo-1H,8H-
indazolo[2,3,4-cde]benzotriazol-9-ium hydroxide}, bis(inner salt), tetrasodium salt of the formula indazolo-[2,3,4-cde]benzotriazol-9-ium hydroxide}, bis (inner salt), tetrasodium salt.

This invention is also concerned with a method of inhibiting the complement system in a body fluid, such as blood serum, which comprises subjecting body fluid complement to the action of an effective complement inhibiting amount of a compound encompassed within formula (I) hereinabove. The method of use aspect of this invention is also concerned with a method of inhibiting the complement system in a warm-blooded animal which comprises internally administering to said animal an effective complement inhibiting amount of a compound encompassed within formula (I) hereinabove. Body fluid can include blood, plasma, serum, synovial fluid, cerebrospinal fluid, or pathological accumulations of fluid such as pleural effusion, etc.

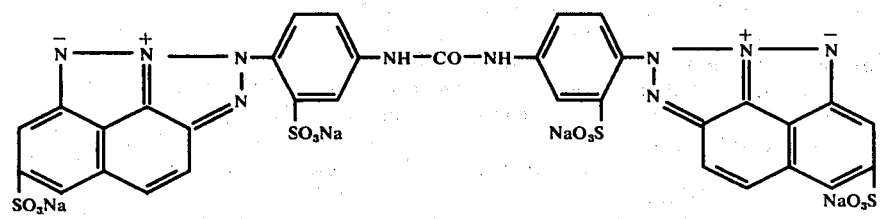

Representative salts encompassed within this invention include, for example, the salt of the formula:

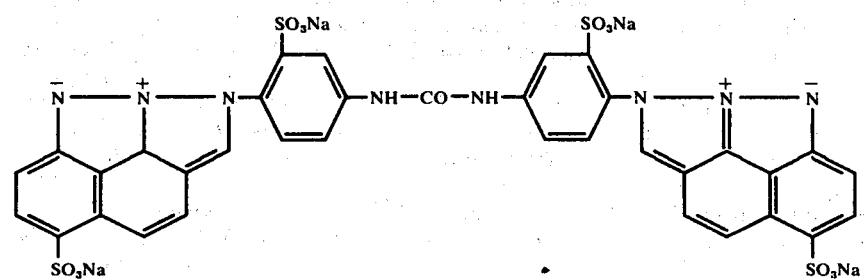

A compound related to those of the present invention, and disclosed as having anticomplementary effect, is the compound 3,3'-ureylenebis[6-(2-amino-8-hydroxy-6-sulfo--1-naphthylazo)]benzenesulfonic acid tetrasodium salt(chlorazol fast pink), British Journal of Experimental Pathology, 33, 327–339 (1952).

The compounds of this invention may be prepared, for example, by treatment of a 4,6-diamino-5-(4-amino-2-sulfophenylazo)naphthalenesulfonic acid, disodium salt with phosgene to provide a 5,5'-[ureylenebis(2-sulfo-p-phenyleneazo)]bis[4,6--diaminonaphthalenesulfonic acid] tetrasodium salt. Reaction of the latter with formic acid-sodium nitrate followed by sodium azide at −5° C produce the compounds of the invention, 1,1'--[ureylenebis(2-sulfo-p-phenylene)]bis{sulfo-1H,8H-

The compounds of the present invention find utility as complement inhibitors in body fluids and as such may be used to ameliorate or prevent those pathological reactions requiring the function of complement and in the therapeutic treatment of warm-blooded animals having immunologic diseases such as rheumatoid arthritis, systemic lupic erythematosus, certain kinds of glomerulonephritis, certain kinds of auto-allergic hemolytic anemia, certain kinds of platelet disorders and certain kinds of vasculitis. The compounds herein may also be used in the therapeutic treatment of warm-blooded animals having non-immunologic diseases such as paroxysmal nocturnal hemoglobinuria, hereditary angioneurotic edema (treated with Suramin Sodium, etc.) and inflammatory states induced by the action of bacterial of lysosomal enzymes on the appropriate complement components as for example, inflammation following coronary occlusion. They may also be useful in the treatment of transplant rejection.

DETAILED DESCRIPTION OF THE INVENTION

The following examples will serve to illustrate the invention in more detail.

EXAMPLE 1

1,1'-[Ureylenebis(2-sulfo-p-phenylene)]bis{6-sulfo--1H,8H-indazolo[2,3,4-cde]benzotriazol-9-ium hydroxide}, bis(inner salt), tetrasodium salt A solution of 67 g of 6-amino-2-naphthalenesulfonic acid in 375 ml of concentrated sulfuric acid is prepared by warming. This solution is then cooled to −2° C in an ice-salt bath and 30 g of sodium nitrate is added portionwise over a 10 minute period with stirring. A temperature rise of 5°–18° C is anticipated. After 15 minutes total stirring the mixture is poured over one liter of crushed ice. The mixture is filtered through diatomaceous earth and the residue is washed with water. The product is dissolved on the filter with approximately 250 ml of 2.2 N sodium hydroxide and the filtrate is neutralized with one ml of acetic acid. The solution is concentrated in vacuo to approximately 250 ml and is salted out with 50 g of sodium acetate trihydrate. The mixture is filtered and the product is washed with a 33% aqueous solution of sodium acetate trihydrate followed by ethanol to give 6-amino-4-nitro-2-naphthalenesulfonic acid, sodium salt as red-brown crystals.

A solution of 12.0 g of 2-amino-5-nitrobenzenesulfonic acid sodium salt and 3.5 g of sodium nitrate in 80 ml of water is added to a mixture of 125 ml of crushed ice, 12.5 ml of concentrated hydrochloric acid and 25 ml of acetic acid in an ice-salt bath. The mixture is stirred for approximately 15 minutes then 15.2 g of sodium trihydrate in 25 ml of water is added. This is followed almost immediately by a solution of 14.5 g of 6-amino-4-nitro-2-naphthalenesulfonic acid, sodium salt in 100 ml of water. The mixture is allowed to cool to 0° C and is filtered and washed with a 33% aqueous solution of sodium acetate trihydrate, then with ethanol and ether to give 6-amino-4-nitro-5-(4-nitro-2-sulfophenylazo)-2-naphthalenesulfonic acid, disodium salt, a dark brown powder, as the product.

A 30 g portion of sodium sulfide nonahydrate is added to a solution of 21.4 of the preceding product in 500 ml of water at room temperature and the mixture is stirred at 25–30° C for 20 minutes. A 14.5 ml portion of acetic acid is added, the mixture is concentrated to 300 ml and is filtered through diatomaceous earth. The filtrate is concentrated further to 160 ml and the mixture is stirred for 2 hours to complete crystallization of the product. The mixture is filtered and the product is washed with a 33% aqueous solution of sodium acetate trihydrate, then with ethanol and ether. The brown powder obtained is 4,6-diamino-5-(4-amino-2-sulfophenylazo)-2-naphthalenesulfonic acid, disodium salt.

Phosgene is bubbled through a solution of 12.1 g of the above product and 5.0 of anhydrous sodium carbonate in 120 ml of water at room temperature until electrophoresis indicates that the reaction is complete. The product is salted out with 60 g of sodium acetate trihydrate and is washed with a 33% aqueous solution of sodium acetate trihydrate, then with ethanol and ether to give 5,5'-[ureylenebis(2-sulfo-p-phenyleneazo)]bis[4,6-diamino-2-naphthalenesulfonic acid], tetrasodium salt as a dark red powder.

To a solution of 1.08 g of the above product in 10 ml of water and 3 ml of 88% formic acid, cooled to approximately −5° C in an ice-salt bath, is added a solution of 300 mg of sodium nitrite in one ml of water. After stirring approximately 5 minutes a solution of 650 mg of sodium azide in 2 ml of water is added to the thick purple mixture. A vigorous evolution of gas occurs to give a brown solution which is stirred at room temperature for 30 minutes. The solution is concentrates in vacuo to 6.5 ml and is salted out with 4.0 g of sodium acetate trihydrate. The mixture is filtered and the residue is washed with a 33% aqueous solution of sodium acetate. The aqueous filtrate containing the washings is poured into 150 ml of ethanol. This mixture is filtered and the product is washed with ethanol and ether to give a mixture of product and sodium formate. This material is dissolved in 5 ml of water and acidified with 3.4 g of 70% perchloric acid. The solution is poured into 75 ml of ethanol and the mixture is filtered. The product is washed with ethanol and ether to give 1,1'-[ureylenebis(2-sulfo-p-phenylene)]bis{6-sulfo-1H,8H-indazolo[2,3,4-cde]benzotriazol-9-ium hydroxide}, bis(inner salt), tetrasodium salt.

Example 2

Preparation of Compressed Tablet

| | mg./tablet |
|---|---|
| 1,1'-[Ureylenebis(2-sulfo-p-phenylene)]bis{6-sulfo-1H,8H-indazolo[2,3,4-cde]benzotriazol-9-ium hydroxide}, bis(inner salt), tetrasodium salt | 0.5 – 500 |
| Dibasic Calcium Phosphate NF | qs |
| Starch USP | 40 |
| Modified Starch | 10 |
| Magnesium Stearate USP | 1 – 5 |

Example 3

Preparation of Compresses Tablet-Sustained Action

| | mg./tablet |
|---|---|
| 1,1'-[Ureylenebis(2-sulfo-p-phenylene)]bis{6-sulfo-1H,8H-indazolo[2,3,4-cde]-benzotriazol-9-ium hydroxide}, bis(inner salt), tetrasodium salt as aluminum lake,* micronized | 0.5 – 500 as acid equivalent |
| Dibasic Calcium Phosphate NF | qs |
| Alginic Acid | 20 |
| Starch USP | 35 |
| Magnesium Stearate USP | 1 – 10 |

*Complement inhibitor as sodium salt plus aluminum sulfate yields aluminum complement inhibitor. Complement inhibitor content in aluminum lake ranges from 5–30%.

Example 4

Preparation of Hard Shell Capsule

| Preparation of Hard Shell Capsule | |
|---|---|
| | mg./tablet |
| 1,1'-[Ureylenebis(2-sulfo-p-phenylene)]bis{6-sulfo-1H,8H-indazolo[2,3,4-cde]benzotriazol-9-ium hydroxide}, bis(inner salt), tetrasodium salt | 0.5 – 500 |
| Lactose, Spray dried | qs |
| Magnesium Stearate | 1 – 10 |

Example 5

Preparation of Oral Liquid (Syrup)

| | mg./tablet |
|---|---|
| 1,1'-[Ureylenebis(2-sulfo-p-phenylene)]bis{6-sulfo-1H,8H-indazolo[2,3,4-cde]benzotriazol-9-ium hydroxide}, bis(inner salt), tetrasodium salt | 0.05 – 5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

Example 6

Preparation of Oral Liquid (Elixir)

| | % w/v |
|---|---|
| 1,1'-[Ureylenebis(2-sulfo-p-phenylene)]bis{6-sulfo-1H,8H-indazolo[2,3,4-cde]benzotriazol-9-ium hydroxide}, bis(inner salt), tetrasodium salt | 0.05 – 5 |
| Alcohol USP | 12.5 |
| Glycerin USP | 45.0 |
| Syrup USP | 20.0 |
| Flavoring Agent | qs |
| Purified Water qs ad | 100.0 |

Example 7

Preparation of Oral Suspension (Syrup)

| | % w/v |
|---|---|
| 1,1'-[Ureylenebis(2-sulfo-p-phenylene)]bis{6-sulfo-1H,8H-indazolo[2,3,4-cde]benzotriazol-9-ium hydroxide}, bis(inner salt), tetrasodium salt as aluminum lake, micronized | 0.05 – 5 (acid equivalent) |
| Polysorbate 80 USP | 0.1 |
| Magnesium Aluminum Silicate Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

Example 8

Preparation of Injectable Solution

| | % w/v |
|---|---|
| 1,1'-[Ureylenebis(2-sulfo-p-phenylene)]bis{6-sulfo-1H,8H-indazolo[2,3,4-cde]benzotriazol-9-ium hydroxide}, bis(inner salt), tetrasodium salt | 0.05 – 5 |
| Benzyl Alcohol N.F. | 0.09 |
| Water for Injection | 100.0 |

Example 9

Preparation of Injectable Oil

| | % w/v |
|---|---|
| 1,1'-[Ureylenebis(2-sulfo-p-phenylene)]bis{6-sulfo-1H,8H-indazolo[2,3,4-cde]benzotriazol-9-ium hydroxide}, bis(inner salt), tetrasodium salt | 0.05 – 5 |
| Benzyl Alcohol | 1.5 |
| Sesame Oil qs ad | 100.0 |

Example 10

Preparation of Injectable Depo Suspension

| | % w/v |
|---|---|

Example 10-continued

Preparation of Injectable Depo Suspension

| | |
|---|---|
| 1,1'-[Ureylenebis(2-suflo-p-phenylene)]bis{6-sulfo-1H,8H-indazolo[2,3,4-cde]benzotriazol-9-ium hydroxide}, bis(inner salt), tetrasodium salt as aluminum lake, micronized | 0.05 – 5 (acid equivalent |
| Polysorbate 80 USP | 0.2 |
| Polyethylene Glycol 400 USP | 3.0 |
| Sodium Chloride USP | 0.8 |
| Benzyl Alcohol N.F. | 0.9 |
| HCl to pH 6 – 8 | qs |
| Water for Injection qs ad | 100.0 |

The compounds of this invention may be administered internally, e.g., orally or parenterally, e.g., intra-articularly, to a warm-blooded animal to inhibit complement in the body fluid of the animal, such inhibition being useful in the amelioration of prevention of those reactions dependent upon the function of complement, such as inflammatory process and cell membrane damage induced by antigen-antibody complexes. A range of doses may be employed depending on the mode of administration, the condition being treated and the particular salt being used. For example, for intravenous or subcutaneous use from about 5 to about 50 mg./kg./day, or every six hours for more rapidly excreted salts, may be used. For intra-articular use for large joints such as the knee, from about 2 to about 20 mg./joint per week may be used, with proportionally smaller doses for smaller joints. The dosage range is to be adjusted to provide optimum therapeutic response in the warm-blooded animal being treated. In general, the amount of salt administered can vary over a wide range to provide from about 5 mg./kg. to about 100 mg./kg. of body weight of animal per day. The usual daily dosage for a 70 kg. subject may vary from about 350 mg. to about 3.5 g. Unit doses of the salt can contain from about 0.5 mg. to about 500 mg.

In therapeutic use the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety for forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage, an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The Tablet or pill may be colored through the use of appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form as described herein refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powders, packets, granules, wafers, cachets, teaspoonfuls, dropperfuls, ampules, vials, segregated multiples of any of the foregoing and other forms as herein described.

The complement inhibiting activity of a representative compound of this invention has been demonstrated by one or more of the following identified tests: (i) Test, Code 026 (C1 inhibitor). This test measures the ability of activated human C1 to destroy fluid phase human C2 in the presence of C4 and appropriate dilutions of the test compound. An active inhibitor protects C2 from C1 and C4; (ii) Test, Code 035 (c3–C9 inhibitor) - This test determines the ability of the late components of human complement (C3–C9) the lyse EAC 142 in the presence of appropriate dilutions of the test compound. An active inhibitor protects EAC 142 from lysis by human C3–C9; (iii) Test Code 036 (C-Shunt inhibitor)-In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test -Here, the well complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg./kg. is then reported, unless otherwise states; (v) Forssman Shock Test - Lethal shock is produced in guinea pigs by an i.v. injection of anti-Forssman antiserum and the harmonic mean death time of treated guinea pigs is compared with that of simultaneous controls; (vi) Complement Level Reduction Test - In this test, the above dosed guinea pigs, or others, are bled for serum and the complement level is determined in undiluted serum by the capillary tube method of U.S. Pat. No. 3,876,376 and compared to undosed control guinea pigs; and (vii) Cap 50 Test - Here, appropriate amounts of the test compound are added to a pool of guinea pig serum in vitro, after which the undiluted serum capillary tube assay referred to above is run. The concentration of compound inhibiting 50% is reported.

Table I shows that the principal compound of the invention has significant anti-complement activity.

TABLE I

| | Biological Activities | | | |
| --- | --- | --- | --- | --- |
| | Assay Results | | | |
| | In Vitro | | In Vivo | |
| Compound | 026* | 035 | Forssman | % Reduction Complement |
| 1,1'-[Ureylenebis(2-sulfo-p-phenylene)]bis{6-sulfo-1H,8H-indazolo[2,3,4-cde]benzotriazol-9-ium hydroxide}, bis(inner salt), tetrasodium salt | +4** | +1 | 25 | 15 |

*Test identified by code herein.
**Activity 4 wells, a serial dilution assay; higher well number indicates higher activity. The serial dilutions are two-fold.

We Claim:
1. A compound selected from those of the formula:

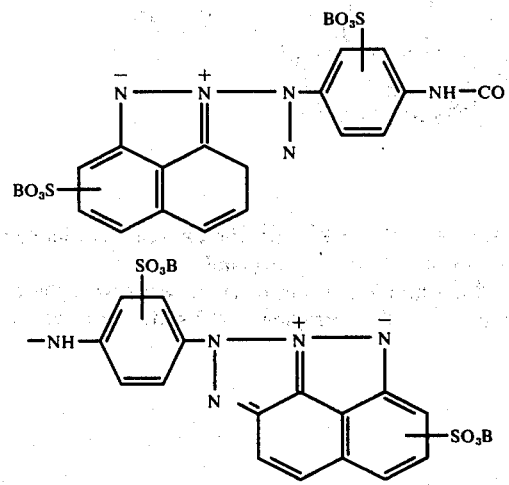

wherein B is Na or K, with the proviso that each B is identical to the same compound.
2. A compound selected from those of the formula:

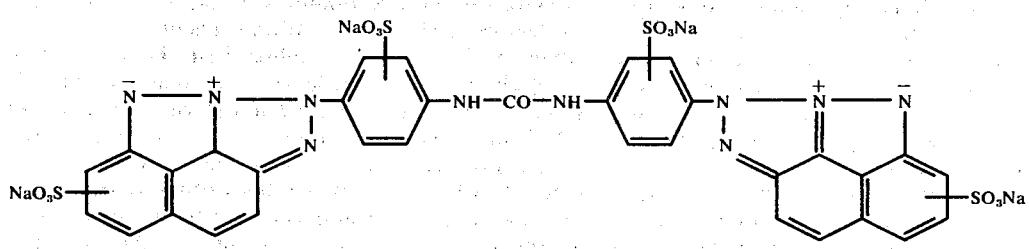

3. A compound according to claim 2, 1,1'-[ureylenebis(2-sulfo-p-phenylene)]bis{6-sulfo-1H,8H-indazolo[2,3,4-cde]-benzotriazol-9-ium hydroxide}, bis (inner salt), tetrasodium salt of the formula

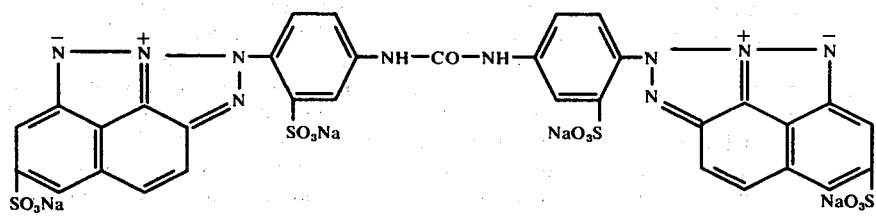

4. A method of inhibiting the complement system in a body fluid which comprises subjecting said body fluid to the action of an effective complement inhibiting amount of a compound of the formula:

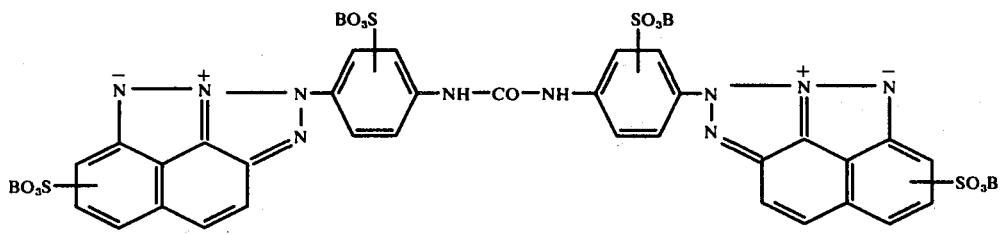

wherein B is Na or K, with the proviso that each B is identical in the same compound.

5. A method according to claim 4 wherein the compound is 1,1'-[ureylenebis(2-sulfo-p-phenylene)]-bis{6-sulfo-1H,8H-indazolo[2,3,4-cde]benzotriazol-9-ium hydroxide}, bis-(inner salt), tetrasodium salt.

6. A method of inhibiting the complement system in a warm-blooded animal which comprises internally administering to said animal an effective complement inhibiting amount of a compound of the formula:

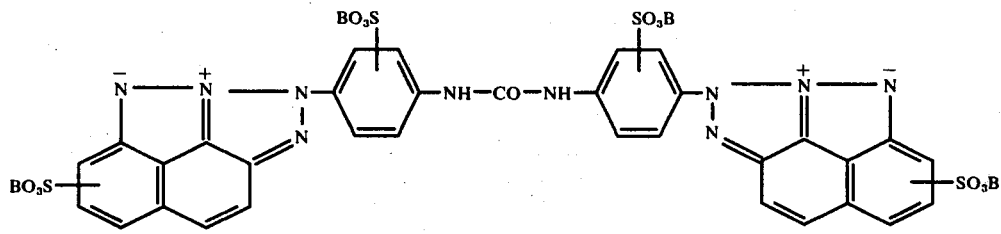

wherein B is Na or K, with the proviso that each B is identical in the same compound.

7. A method according to claim 6 wherein the compound of 1,1'-[ureylenebis(2-sulfo-p-phenylene)]bis{6-sulfo-1H,8H-indazolo[2,3,4-cde]benzotriazol-9-ium hydroxide}, bis- (inner salt), tetrasodium salt.

* * * * *

UNITED STATES PATENT OFFICE
CERTIFICATE OF CORRECTION

Patent No. 3,998,957                 Dated December 21, 1976

Inventor(s) RANSOM BROWN CONROW and SEYMOUR BERNSTEIN

It is certified that error appears in the above-identified patent and that said Letters Patent are hereby corrected as shown below:

Claim 1, change --

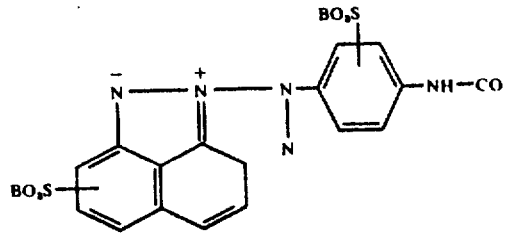

to --

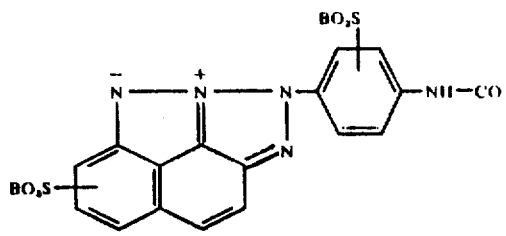

Claim 2, change --

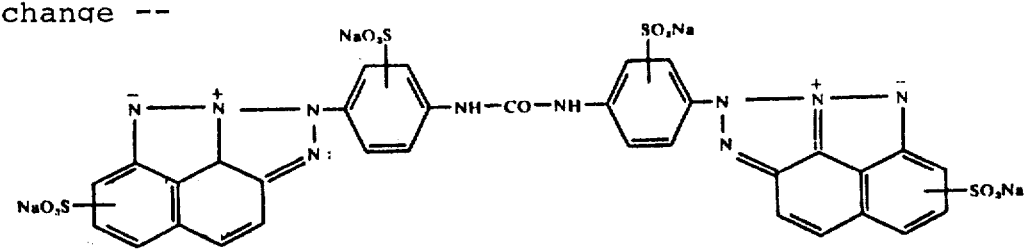

to --

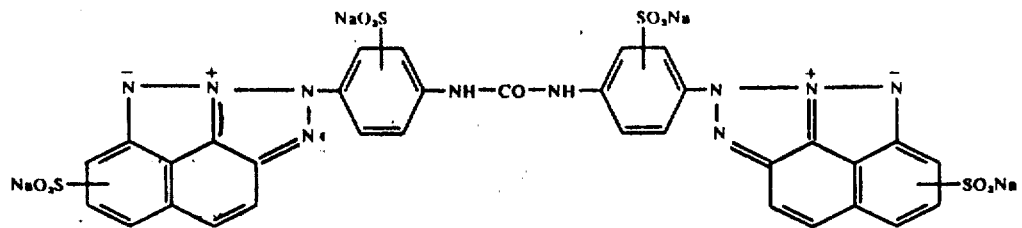

Signed and Sealed this

Twenty-ninth Day of March 1977

[SEAL]

Attest:

RUTH C. MASON
*Attesting Officer*

C. MARSHALL DANN
*Commissioner of Patents and Trademarks*